(12) United States Patent
Halbach et al.

(10) Patent No.: US 9,284,340 B2
(45) Date of Patent: Mar. 15, 2016

(54) OXASILACYCLES AND METHOD FOR THE PRODUCTION THEREOF

(71) Applicant: Wacker Chemie AG, Munich (DE)

(72) Inventors: Tobias Halbach, Munich (DE); Juergen Stohrer, Pullach (DE); Bernhard Rieger, Elchingen (DE); Christian Anger, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/413,584

(22) PCT Filed: Jul. 2, 2013

(86) PCT No.: PCT/EP2013/063921
§ 371 (c)(1),
(2) Date: Jan. 8, 2015

(87) PCT Pub. No.: WO2014/009204
PCT Pub. Date: Jan. 16, 2014

(65) Prior Publication Data
US 2015/0183808 A1 Jul. 2, 2015

(30) Foreign Application Priority Data
Jul. 11, 2012 (DE) .......................... 10 2012 013 711

(51) Int. Cl.
*C07F 7/18* (2006.01)
*C07F 7/08* (2006.01)

(52) U.S. Cl.
CPC ............ *C07F 7/1868* (2013.01); *C07F 7/0834* (2013.01); *C07F 7/184* (2013.01); *C07F 7/1892* (2013.01)

(58) Field of Classification Search
USPC ................................. 556/464, 478, 479, 482
See application file for complete search history.

(56) References Cited

U.S. PATENT DOCUMENTS

| 4,528,389 | A | 7/1985 | Farnham |
|---|---|---|---|
| 5,274,053 | A | 12/1993 | Kurata et al. |
| 5,786,493 | A | 7/1998 | Rauleder et al. |
| 2001/0011120 | A1 | 8/2001 | Okawa et al. |
| 2004/0073031 | A1 | 4/2004 | Schafer et al. |
| 2006/0040897 | A1 | 2/2006 | Friedman et al. |
| 2007/0055036 | A1 | 3/2007 | Nagy |
| 2009/0050020 | A1 | 2/2009 | Konno et al. |
| 2009/0298980 | A1 | 12/2009 | Yoshitake et al. |
| 2010/0331483 | A1 | 12/2010 | Briehn et al. |
| 2012/0220793 | A1 | 8/2012 | Daiss et al. |
| 2013/0018200 | A1 | 1/2013 | Daiss et al. |
| 2013/0078333 | A1 | 3/2013 | Kumazawa et al. |
| 2013/0345370 | A1 | 12/2013 | Ona et al. |

FOREIGN PATENT DOCUMENTS

| DE | 19628588 A1 | 1/1998 |
|---|---|---|
| DE | 10109842 A1 | 10/2002 |
| DE | 102004029259 A1 | 1/2006 |
| DE | 102006048217 A1 | 4/2008 |
| DE | 102008000353 A1 | 8/2009 |
| DE | 102009046254 A1 | 5/2011 |
| DE | 102010003108 A1 | 9/2011 |
| EP | 0110370 B1 | 6/1984 |
| EP | 0629648 A2 | 12/1994 |
| JP | 7-149901 | 6/1995 |
| JP | 2000186103 A | 7/2000 |
| WO | 03014167 A1 | 2/2003 |
| WO | 2005044828 A1 | 5/2005 |
| WO | 2011051108 A1 | 5/2011 |

OTHER PUBLICATIONS

Shchepin; Organic Letters, 2010, vol. 12, No. 21, 4772-4775.*
W. Noll, "Chemie and Technologie der Silicone," Verlag Chemie GmbH, 1968, pp. 9 (and Abstract).
S. Denmark et al., "A Stereochemical Study on the Intramolecular Hydrosilylation of a,ss-Unsaturated Esters," Tetrahedron Letters, vol. 33, No. 35, pp. 5037-5040, 1992.
R. Shchepin et al, "B(C6F5)3-Promoted Tandem Silyltation and Intramolecular Hydrosilylation: Diastereoselective Synthesis of Oxasilinanes and Oxaselepanes", Organic Letters, 2010 vol. 12, pp. 4772-4775.
X. Baopei et al, "Spiro(benzoxasilole) Catalyzed Polymerization of Oxetane Derivatives", Journal of Polymer Science, Part A: Polymer Chemistry, 30(0), 1899-909 CODEN: JPACEC; ISSN 0887-624X; 1992, XP0027-12461.
E.T. Denisov et al., "Handbook of Free Radical Initiators," published by John Wiley & Sons, Inc., 2003.

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Oxasilacycles are prepared by the intramolecular condensation of silanes bearing Si-bonded hydrogen and ethylenically unsaturated radicals in the presence of a triorganoborane, aminoborane complex, or phosphine-borane complex as a hydrosilylation catalyst. Spirocyclic oxasilacycles, and alkoxy-substituted oxaspirocycles with quaternary substitution of a C atom adjacent to oxygen may be prepared.

17 Claims, No Drawings

OXASILACYCLES AND METHOD FOR THE PRODUCTION THEREOF

CROSS REFERENCE TO RELATED APPLICATIONS

This application is the U.S. National Phase of PCT Appln. No. PCT/EP2013/063921 filed 2 Jul., 2013, which claims priority to German Application No. 10 2012 013 711.7 filed Jul. 11, 2012, the disclosures of which are incorporated in their entirety by reference herein.

BACKGROUND OF THE INVENTION

1. Field of the Invention

The invention relates to innovative oxasilacycles and to their preparation.

2. Description of the Related Art

DE102008000353A1 describes crosslinkable polymer blends which comprise at least one alkoxysilyl group of the type $\equiv$Si—O—C($R^1$)($R^2$)($R^3$), and the use thereof for anhydrous silane crosslinking.

Organic Letters 2010, 12, 4772-4775 describes a synthesis for oxasilinanes and oxasilepanes by means of intramolecular hydrosilylation. Structures with quaternary substitution of the C atom adjacent to the oxygen are not described.

DE 19628588A1 describes cyclic silane esters and products of their solvolysis, and also processes for preparing the cyclic silane esters and the solvolysis products. The preparation is via a hydrogensilane, which is converted into a cyclic organosilane ester in a hydrosilylation reaction via the stage of the organohydrogensilane ester.

Tetrahedron Letters 1992, 33, 5037 describes intramolecular hydrosilylation to form 5-membered rings, using Pt catalysts. DE102006048217 and DE102010003108 describe the preparation of cyclic alkoxysilanes. In this case, however, no spirocyclic silanes or alkoxy-substituted oxasilacycles are described.

Spirocyclic oxasilacycles and alkoxy-substituted oxasilacycles with quaternary substitution of the C atom adjacent to the oxygen, prepared via an intramolecular hydrosilylation, are not mentioned.

SUMMARY OF THE INVENTION

Provided by this invention are oxasilacycles of the general formulae (1) and (2)

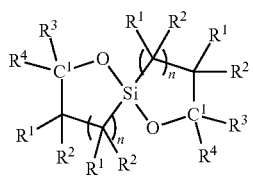

(1)

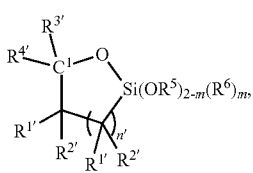

(2)

in which $R^1$, $R^2$, $R^{1'}$, and $R^{2'}$ are hydrogen, halogen, cyano, OH, or unsubstituted or substituted hydrocarbyloxy radical, acyloxy radical, alkoxy radical or hydrocarbyl radical having in each case 1 to 50 carbon atoms, in each of which nonadjacent carbon atoms may be replaced by heteroatoms selected from N, O, P, and S, where two or three of the radicals $R^1$, $R^2$, $R^{1'}$, and $R^{2'}$ may be joined to one another, $R^3$, $R^4$, $R^{3'}$, and $R^{4'}$ are unsubstituted or substituted hydrocarbyl radicals having in each case 1 to 50 carbon atoms, in each of which nonadjacent carbon atoms may be replaced by heteroatoms selected from N, O, P, and S, or is a high molecular mass radical, $R^5$, and $R^6$ are unsubstituted or substituted hydrocarbyl radicals having in each case 1 to 50 carbon atoms, in each of which nonadjacent carbon atoms may be replaced by heteroatoms selected from N, O, P, and S, m is 0 or 1, and n, and n' are integers of at least 1.

DETAILED DESCRIPTION OF THE PREFERRED EMBODIMENTS

The oxasilacycles of the general formulae (1) and (2) are notable for the presence in the cyclic moiety of an Si—O—C bond, in which the C atom has quaternary substitution, and the compound in question in each case is a spirocyclic compound of the formula (1) or a cyclic compound of the formula (2) with at least one further hydrocarbyloxy group.

The unsubstituted or substituted hydrocarbyloxy radicals, acyloxy radicals, alkoxy radicals, or hydrocarbyl radicals each have preferably 1 to 12 carbon atoms, more particularly 1 to 6 carbon atoms.

Examples of hydrocarbyl radicals are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; aryl radicals such as the phenyl, naphthyl, anthryl, and phenanthryl radicals; alkaryl radicals such as the o-, m-, and p-tolyl radicals, xylyl radicals and ethylphenyl radicals; and aralkyl radicals such as the benzyl radical, and the α- and the β-phenylethyl radicals.

The substituents on the hydrocarbyl radicals $R^3$, $R^4$, $R^{3'}$, $R^{4'}$, $R^5$, and $R^6$ may be, for example, halogens, such as fluorine, chlorine, or bromine, or cyano radicals.

The radicals $R^3$ and $R^4$ and $R^{3'}$ and $R^{4'}$ preferably have 1 to 12, more preferably 1 to 6, carbon atoms. Also preferred are high molecular mass radicals which preferably have (polymeric) repeating units, e.g. are organic polymers.

With particular preference the radicals $R^3$ and $R^4$ and $R^{3'}$ and $R^{4'}$ are methyl, ethyl, propyl, butyl, vinyl, phenyl, or carboxyl radicals —C(O)OCH$_3$.

The cyclic moieties in the oxasilacycles of the general formulae (1) and (2) have at least a 5-membered ring (n, n'=1), preferably a 6- or 7-membered ring (n, n'=2, 3). The oxasilacycles of the general formulae (1) and (2) have either two cyclic moieties (formula (1)) or one cyclic moiety (formula (2)).

Oxasilacycles of the general formula (2) preferably have at least one OR$^5$ group, in which R$^5$ is preferably an alkyl or aryl group. $R^6$ is preferably an alkyl, carbonyl, or aryl group, such as methyl, ethyl, propyl, phenyl, methoxy, ethoxy, or acetoxy, for example.

Examples of preferred structures are as follows:
a) n=2; $R^1$, $R^2$=H; $R^3$, $R^4$=CH$_3$
b) n=3; $R^1$, $R^2$=H; $R^3$, $R^4$=CH$_3$
c) n'=2; $R^{1'}$, $R^{2'}$=H; $R^{3'}$, $R^{4'}$=CH$_3$; m=1; $R^5$=CH$_3$, $R^6$=CH$_3$
d) n'=2; $R^{1'}$, $R^{2'}$=H; $R^{3'}$, $R^{4'}$=CH$_3$; m=1; $R^5$=C$_2$H$_5$, $R^6$=CH$_3$
e) n'=2; $R^{1'}$, $R^{2'}$=H; $R^{3'}$, $R^{4'}$=CH$_3$; m=1; $R^5$=C$_2$H$_5$, $R^6$=C$_2$H$_5$
f) n'=2; $R^{1'}$, $R^{2'}$=H; $R^{3'}$, $R^{4'}$=CH$_3$; m=1; $R^5$=i-C$_3$H$_7$, $R^6$=CH$_3$
g) n'=2; $R^{1'}$, $R^{2'}$=H; $R^{3'}$, $R^{4'}$=CH$_3$; m=0; $R^5$=CH$_3$
h) n'=2; $R^{1'}$, $R^{2'}$=H; $R^{3'}$, $R^{4'}$=CH$_3$; m=0; $R^5$=C$_2$H$_5$.

Further provided by the invention is a process for preparing oxasilacycles of the general formula (1) from compounds of the general formula (3),

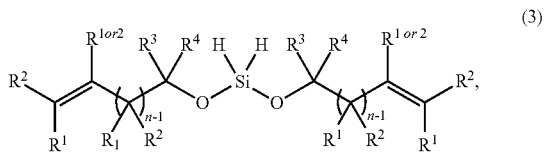

and a process for preparing oxasilacycles of the general formula (2) from silanes of the general formula (4),

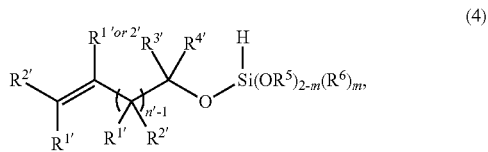

wherein the silanes of the general formulae (3) or (4) are reacted in the presence of hydrosilylation catalysts.

The silanes of the general formulae (3) or (4) may be prepared by using commonplace methods familiar to the skilled person. For example, chlorosilanes can be reacted with corresponding alcohols containing a terminal double bond, with the ring closure carried out subsequently by intramolecular hydrosilylation.

Oxasilacycles of the general formulae (1) or (2) may be prepared by intramolecular hydrosilylation using hydrosilylation catalysts known to the skilled person. Preference is given to using platinum metals or compounds thereof; triorganoboranes $BR_3$; aminoborane complexes $R_3NBH_3$; or phosphine-boranes $R_3PBH_3$, where R is a hydrocarbyl radical which is unsubstituted or substituted by halogen atoms and which has in each case 1 to 12 carbon atoms, as a catalyst.

Preferred as platinum metals and compounds thereof are platinum and/or its compounds. Here it is possible to use all catalysts which have also been used to date for the addition of hydrogen atoms bonded directly to Si atoms onto aliphatically unsaturated compounds. Examples of such catalysts are metallic and finely divided platinum, which may be accommodated on supports, such as silicon dioxide, aluminum oxide, or activated carbon; compounds or complexes of platinum, such as platinum halides, e.g., $PtCl_4$, $H_2PtCl_6 \cdot 6H_2O$, $Na_2PtCl_4 \cdot 4H_2O$, platinum-olefin complexes, platinum-alcohol complexes, platinum-alkoxide complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, more particularly platinum-divinyltetramethyldisiloxane complexes with or without detectable inorganically bonded halogen, bis(gamma-picoline)platinum dichloride, trimethylenedipyridineplatinum dichloride, dicyclopentadieneplatinum dichloride, dimethyl sulfoxide-ethyleneplatinum(II) dichloride, and also reaction products of platinum tetrachloride with olefin and with primary amine or secondary amine or primary and secondary amine, such as the reaction product of platinum tetrachloride in solution in 1-octene with sec-butylamine, or ammonium-platinum complexes as per EP-B 110 370.

Palladium and/or its compounds such as tetrakistriphenylphosphinepalladium(0), for example, are likewise suitable.

The platinum catalyst is preferably used in amounts of 0.5 to 500 ppm by weight (parts by weight per million parts by weight), more preferably 2 to 300 ppm by weight, calculated in each case as elemental platinum and based on the weight of the silanes of the general formulae (3) or (4).

Examples of aminoborane complexes $R_3NBH_3$ are trimethylamine-borane, triethylamine-borane, tricyclopentylamine-borane, triphenylamine-borane, or dimethylbenzylamine-borane.

Examples of phosphine boranes $R_3PBH_3$ are trimethylphosphine borane, tributylphosphine borane, or triphenylphosphine borane.

An example of a triorganoborane $BR_3$ is $B(C_6F_5)_3$.

R is preferably a hydrocarbyl radical which is substituted by fluorine or chlorine, more particularly a perfluorinated hydrocarbyl radical. Used with particular preference as a catalyst is $B(C_6F_5)_3$.

Triorganoboranes $BR_3$ are preferably used in amounts of 0.1 to 10 mol %, more preferably 0.5 to 5 mol %, based in each case on the silanes of the general formulae (3) or (4).

The temperature for the intramolecular hydrosilylation is preferably −80° C. to 120° C., more preferably −10° C. to 50° C., and most preferably 0° C. to 30° C.

The intramolecular hydrosilylation may be carried out in the presence or in the absence of aprotic solvents. If aprotic solvents are used, preferred solvents or solvent mixtures are those having a boiling point or boiling range, respectively, of up to 120° C. at 0.1 MPa. Examples of such solvents are ethers such as dioxane, tetrahydrofuran, diethyl ether, diisopropyl ether, and diethylene glycol dimethyl ether; chlorinated hydrocarbons such as dichloromethane, trichloromethane, tetrachloromethane, 1,2-dichloroethane, and trichloroethylene; hydrocarbons such as pentane, n-hexane, hexane isomer mixtures, heptane, octane, wash benzene, petroleum ether, benzene, toluene, and xylenes; siloxanes, more particularly linear dimethylpolysiloxanes having trimethylsilyl end groups, with preferably 0 to 6 dimethylsiloxane units, or cyclic dimethylpolysiloxanes with preferably 4 to 7 dimethylsiloxane units, examples being hexamethyldisiloxane, octamethyltrisiloxane, octamethylcyclotetrasiloxane, and decamethylcyclopentasiloxane; ketones such as acetone, methyl ethyl ketone, diisopropyl ketone, and methyl isobutyl ketone (MIBK); esters such as ethyl acetate, butyl acetate, propyl propionate, ethyl butyrate, and ethyl isobutyrate; carbon disulfide; and nitrobenzene, or mixtures of these solvents.

The oxasilacycles find application for the modification and crosslinking of siloxanes and organic polymers. Cyclic structures such as, for example, 2-isopropoxy-2,6,6-trimethyl-1,2-oxasilinane may be used for preparing new polymerizable and crosslinkable telechelic structures. Without addition of catalysts, these structures react with hydroxy terminated polydimethylsiloxanes to form the telechele.

The oxasilacycles of the general formulae (1) and (2) are notable in that with catalysts (K) a ring opening is achieved, with formation of silanol groups ≡Si—OH and terminal double bonds. One example of this is the following structure, formed by the ring opening of 2,2,8,8-tetramethyl-1,7-dioxa-6-silaspiro[5.5]undecane:

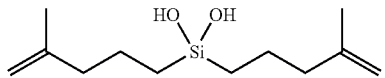

In contrast to DE102008000353A1, no vinyl-functional compound is released as a low molecular mass elimination product. After ring opening, the vinyl-functional compound remains on the Si atom.

With particular preference the ring opening takes place without ingress of (atmospheric) moisture.

Preferred catalysts (K) are Lewis acids and Brønsted acids.

All of the above symbols in the above formulae have their definitions in each case independently of one another.

Unless otherwise indicated, all quantity and percentage figures in the examples hereinafter are given by weight, all pressures are 0.10 MPa (abs.), and all temperatures are 20° C.

Example 1

Synthesis of bis((2-methylpent-4-en-2-yl)oxy)silane (3)

A heat-dried three-neck Schlenk flask with reflux condenser and dropping funnel is charged with 250 mL of dry diethyl ether and then about 25 ml of the mixture in the dropping funnel are added, this mixture consisting of 31.9 g (389 mmol) of 1-methylimidazole and 38.9 g (389 mmol) of 2-methylpent-4-en-2-ol in 50 mL of diethyl ether.

The mixture is then cooled to −78° C. and 19.63 g (194 mmol) of dichlorosilane are diffused in with stirring, the dichlorosilane having been condensed beforehand at −78° C. into a Schlenk tube.

During this procedure, the remaining solution in the dropping funnel is slowly added dropwise, after which the reaction mixture is warmed to room temperature ("RT"). After the mixture has been stirred for 10 hours, the methylimidazole hydrochloride formed is filtered off on a Schlenk frit and the solvent is removed under reduced pressure. Purification is accomplished by fractional condensation (0.3 mbar, oil bath temperature: 60° C.) to give 35.7 g (156 mmol, 81%) of bis((2-methylpent-4-en-2-yl)oxy)silane in the form of a colorless liquid.

$^1$H NMR (300 MHz, CDCl$_3$, 300 K): δ [ppm]=5.97-5.76 (m, 2H, H-3), 5.14-5.00 (H, 4H, H-4), 4.67 (s, 2H, Si—H), 2.29 (d, $^3$J=7.3 Hz, 4H, H-2), 1.3 (s, 12, H-5).

$^{13}$C NMR (75 MHz, CDCl$_3$, 300 K): δ [ppm]=134.8 (s), 117.7 (s), 75.5 (s), 49.0 (s), 29.1 (s, 2C).

MS (EI), m/z (%): 213.16 (13) [(M-CH$_3$)$^+$], 187.13 (100), 129.08 (87) [(M-C$_6$H$_{11}$O)$^+$].

HRMS (C$_{11}$H$_{21}$O$_2$$^{28}$Si=[(M-CH$_3$)$^+$]): calc.: 213.1311. found: 213.1305.

Example 2

Synthesis of 2,2,8,8-tetramethyl-1,7-dioxa-6-silaspiro[5.5]undecane (1)

A heat-dried Schlenk flask is charged with 23.8 g (104 mmol) of bis((2-methylpent-4-en-2-yl)oxy)silane (example 1) in 400 mL of dried dichloromethane, and 1.06 g (2.07 mmol, 2 mol %) of the catalyst B(C$_6$F$_5$)$_3$ are added with stirring at room temperature. The reaction mixture is then stirred at room temperature for 16 hours and purified by fractional condensation.

$^1$H NMR (300 MHz, CDCl$_3$, 300 K): 1.91-1.64 (m, 4H), 1.60-1.38 (m, 4H), 1.29 (s, 6H), 1.20 (s, 6H), 0.68-0.42 (m, 4H).

$^{13}$C NMR (126 MHz, CDCl$_3$, 300 K): 74.4 (s, 2C), 40.9 (s, 2C), 31.7 (s, 2C), 30.2 (s, 2C), 17.8 (s, 2C), 12.1 (s, 2C).

$^{29}$Si NMR (99 MHz, CDCl$_3$, 300 K): 14.41 (s).

MS (EI), m/z (%): 228 (7) [M$^+$], 213 (100), [(M-CH$_3$)$^+$], 186 (19), 129 (26), 127 (23).

HRMS (C$_{12}$H$_{24}$O$_2$$^{28}$Si): calc.: 228.1546. found: 228.1542.

Example 3

Synthesis of methylchloro((2-methylpent-4-en-2-yl)oxy)silane

A heat-dried 1 l Schlenk flask with dropping funnel (250 ml) is charged with 20.00 g (174 mmol) of dichloromethylsilane in 500 ml of dry pentane. In the dropping funnel, 10.97 g (134 mmol) of methylimidazole and 13.39 g (134 mmol) of 2-methylpent-4-en-2-ol are dissolved in 150 ml of dry pentane and added over a time of 1 hour at 0° C. After the mixture has been stirred at 0° C. for 30 minutes, the precipitated methylimidazole hydrochloride is separated off on a Schlenk frit, and the solvent is removed under reduced pressure. Purification is accomplished by distillation under reduced pressure; the product is obtained at 10 mbar and 38° C.

Yield: 19.7 g (110.2 mmol, 68.5%)

$^1$H NMR (500 MHz, CDCl$_3$, 300 K): δ [ppm]=5.93-5.79 (m, 1H), 5.33-5.31 (m, 1H), 5.13-5.05 (m, 2H), 2.33 (d, 2H), 1.35 (s, 6H), 0.52 (s, 3H).

Example 4

Synthesis of 2-isopropoxychloro(2-methylpent-4-en-2-yl)silane (4)

A heat-dried 1 l Schlenk flask with dropping funnel (250 ml) is charged with 4.3 g (24 mmol) of methylchloro((2-methylpent-4-en-2-yl)oxy)silane from example 3 in 500 ml of dry pentane. In the dropping funnel, 1.58 g (19 mmol) of methylimidazole and 1.45 g (24 mmol) of isopropanol are dissolved in 150 ml of dry pentane and added over a time of 1 hour at 0° C. After the mixture has been stirred at 0° C. for 45 minutes, the precipitated methylimidazole hydrochloride is separated off on a Schlenk frit, and the solvent is removed under reduced pressure. The crude product is purified by fractional condensation (oil bath 60° C., receiver N$_2$-cooled, pressure: 0.7-0.2 mbar)

$^1$H NMR (500 MHz, CDCl$_3$, 300 K): δ [ppm]=5.94-5.80 (m, 1H), 5.08-5.02 (m, 2H), 4.73 (d, 1H), 4.16 (sept, 1H), 2.28 (d, 2H), 1.29 (s, 6H), 1.21 (d, 2H).

Example 5

2-Isopropoxy-2,6,6-trimethyl-1,2-oxasilinane (2)

In a heat-dried Schlenk flask, 1.17 g (5.78 mmol) of the 2-isopropoxychloro(2-methylpent-4-en-2-yl)silane from example 4 are admixed with 40 mg (0.08 mmol, 1.4 mol %) of B(C$_6$F$_5$)$_3$ in solution in dichloromethane and this mixture is stirred at RT for 12 hours. The dichloromethane is then removed under reduced pressure (200 mbar) and the crude product is purified by fractional condensation.

$^1$H NMR (300 MHz, CDCl$_3$) δ 4.24-4.06 (m, 1H), 1.88-1.68 (m, 2H), 1.56-1.42 (m, 2H), 1.29 (s, 3H), 1.17 (t, J=5.9 Hz, 6H), 0.74-0.43 (m, 2H), 0.11 (s, 3H).

MS (EI), m/z (%): 187.2 (100) [(M-CH$_3$)$^+$], 160.1 (15), 159.1 (24), 145.1 (28), 143.1 (13) [(M-OCH(CH$_3$)$_2$)$^+$], 117.1 (23).

HRMS (C$_{12}$H$_{24}$O$_2$$^{28}$Si): calc.: 202.1389. found: 202.1381.

The invention claimed is:

1. A process for preparing oxasilacycles of the formulae (1) or (2)

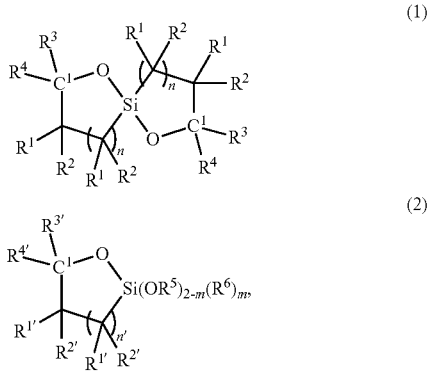

wherein silanes of the formulae (3) or (4), respectively,

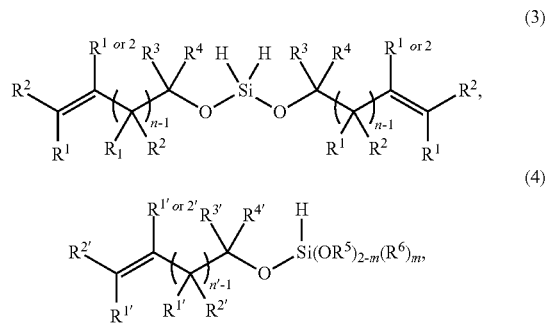

are reacted in the presence of a triorganoborane BR$_3$, aminoborane complex R$_3$NBH$_3$, or phosphine-borane R$_3$PBH$_3$ hydrosilylation catalyst, where R is an C$_{1-12}$ hydrocarbyl radical optionally substituted by halogen atoms, R$^1$, R$^2$, R$^{1'}$, and R$^{2'}$ are hydrogen, halogen, cyano, OH, an optionally substituted C$_{1-50}$ hydrocarbyloxy radical, an optionally substituted C$_{1-50}$ acyloxy radical, or an optionally substituted C$_{1-50}$ hydrocarbyl radical, in which one or more nonadjacent carbon atoms of the optionally substituted C$_{1-50}$ hydrocarbyloxy, C$_{1-50}$ acyloxy, or C$_{1-50}$ hydrocarbyl radicals are optionally replaced by heteroatoms selected from the group consisting of N, O, P, and S, where two or three of the radicals R$^1$, R$^2$, R$^{1'}$, and R$^{2'}$ are optionally joined to one another, R$^3$, R$^4$, R$^{3'}$, and R$^{4'}$ are optionally substituted C$_{1-50}$ hydrocarbyl radicals, in each of which one or more nonadjacent carbon atoms are optionally replaced by heteroatoms selected from the group consisting of N, O, P, and S, or is an organic polymer radical, R$^5$ and R$^6$ are optionally substituted C$_{1-50}$ hydrocarbyl radicals, in each of which one or more nonadjacent carbon atoms are optionally replaced by heteroatoms selected from the group consisting of N, O, P, and S, m is 0, and n, and n' are at least 1.

2. The process of claim 1, in which the radicals R$^3$, R$^4$, R$^{3'}$, and R$^{4'}$ are individually selected from the group consisting of methyl, ethyl, propyl, butyl, vinyl, phenyl, and carboxyl radicals —C(O)OCH$_3$.

3. The process of claim 1, in which n is 1, 2, or 3.

4. The process of claim 2, in which n is 1, 2, or 3.

5. The process of claim 1, in which R$^6$ is selected from the group consisting of methyl, ethyl, propyl, phenyl, methoxy, ethoxy, and acetoxy groups.

6. The process of claim 2, in which R$^6$ is selected from the group consisting of methyl, ethyl, propyl, phenyl, methoxy, ethoxy, and acetoxy groups.

7. The process of claim 3, in which R$^6$ is selected from the group consisting of methyl, ethyl, propyl, phenyl, methoxy, ethoxy, and acetoxy groups.

8. The process of claim 4, in which R$^6$ is selected from the group consisting of methyl, ethyl, propyl, phenyl, methoxy, ethoxy, and acetoxy groups.

9. The process of claim 1, in which the substituents on the hydrocarbyl radicals R$^3$, R$^4$, R$^{3'}$, R$^{4'}$, R$^5$, and R$^6$ are halogen, hydrogen, or cyano radicals.

10. The process of claim 2, in which the substituents on the hydrocarbyl radicals R$^3$, R$^4$, R$^{3'}$, R$^{4'}$, R$^5$, and R$^6$ are halogen, hydrogen, or cyano radicals.

11. The process of claim 3, in which the substituents on the hydrocarbyl radicals R$^3$, R$^4$, R$^{3'}$, R$^{4'}$, R$^5$, and R$^6$ are halogen, hydrogen, or cyano radicals.

12. The process of claim 4, in which the substituents on the hydrocarbyl radicals R$^3$, R$^4$, R$^{3'}$, R$^{4'}$, R$^5$, and R$^6$ are halogen, hydrogen, or cyano radicals.

13. The process of claim 5, in which the substituents on the hydrocarbyl radicals R$^3$, R$^4$, R$^{3'}$, R$^{4'}$, R$^5$, and R$^6$ are halogen, hydrogen, or cyano radicals.

14. The process of claim 6, in which the substituents on the hydrocarbyl radicals R$^3$, R$^4$, R$^{3'}$, R$^{4'}$, R$^5$, and R$^6$ are halogen, hydrogen, or cyano radicals.

15. The process of claim 7, in which the substituents on the hydrocarbyl radicals R$^3$, R$^4$, R$^{3'}$, R$^{4'}$, R$^5$, and R$^6$ are halogen, hydrogen, or cyano radicals.

16. The process of claim 8, in which the substituents on the hydrocarbyl radicals R$^3$, R$^4$, R$^{3'}$, R$^{4'}$, R$^5$, and R$^6$ are halogen, hydrogen, or cyano radicals.

17. A process for preparing oxasilacycles of the formulae (1)

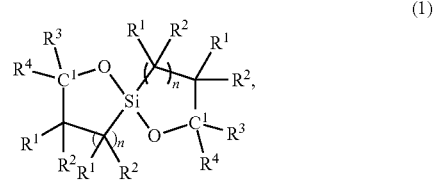

wherein silanes of the formulae (3),

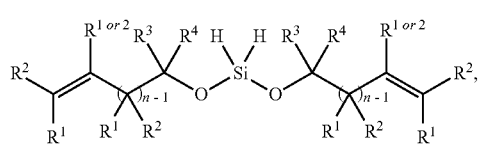

are reacted in the presence of a triorganoborane $BR_3$, aminoborane complex $R_3NBH_3$, or phosphine-borane $R_3PBH_3$ hydrosilylation catalyst,
where
R is an $C_{1-12}$ hydrocarbyl radical optionally substituted by halogen atoms,
$R^1$ and $R^{2'}$ are hydrogen, halogen, cyano, OH, an optionally substituted $C_{1-50}$ hydrocarbyloxy radical, an optionally substituted $C_{1-50}$ acyloxy radical, or an optionally substituted $C_{1-50}$ hydrocarbyl radical, in which one or more nonadjacent carbon atoms of the optionally substituted $C_{1-50}$ hydrocarbyloxy, $C_{1-50}$ acyloxy, or $C_{1-50}$ hydrocarbyl radicals are optionally replaced by heteroatoms selected from the group consisting of N, O, P, and S, where two or three of the radicals $R^1$ and $R^2$ are optionally joined to one another,
$R^3$ and $R^{4'}$ are optionally substituted $C_{1-50}$ hydrocarbyl radicals, in each of which one or more nonadjacent carbon atoms are optionally replaced by heteroatoms selected from the group consisting of N, O, P, and S, or is an organic polymer radical,
$R^5$ and $R^6$ are optionally substituted $C_{1-50}$ hydrocarbyl radicals, in each of which one or more nonadjacent carbon atoms are optionally replaced by heteroatoms selected from the group consisting of N, O, P, and S,
n is at least 1.

* * * * *